(12) United States Patent
Ferreira

(10) Patent No.: US 11,913,960 B2
(45) Date of Patent: Feb. 27, 2024

(54) ELISA ASSAY FOR MEASURING FUNCTION OF PROPERDIN AND KITS FOR CONDUCTING ELISA ASSAYS USING ANTI-PROPERDIN ANTIBODIES

(71) Applicant: The University of Toledo, Toledo, OH (US)

(72) Inventor: Viviana P. Ferreira, Toledo, OH (US)

(73) Assignee: The University of Toledo, Toledo, OH (US)

( * ) Notice: Subject to any disclaimer, the term of this patent is extended or adjusted under 35 U.S.C. 154(b) by 560 days.

(21) Appl. No.: 16/408,621

(22) Filed: May 10, 2019

(65) Prior Publication Data

US 2019/0346451 A1 Nov. 14, 2019

Related U.S. Application Data

(60) Provisional application No. 62/670,314, filed on May 11, 2018.

(51) Int. Cl.
*G01N 33/68* (2006.01)
*G01N 33/543* (2006.01)

(52) U.S. Cl.
CPC .......... *G01N 33/68* (2013.01); *G01N 33/543* (2013.01); *G01N 33/54386* (2013.01); *G01N 2333/4706* (2013.01); *G01N 2333/4716* (2013.01)

(58) Field of Classification Search
None
See application file for complete search history.

(56) References Cited

U.S. PATENT DOCUMENTS

| 4,642,284 A * | 2/1987 | Cooper | G01N 33/537 |
| | | | 435/28 |
| 2013/0004485 A1* | 1/2013 | Bansal | C07K 16/18 |
| | | | 424/133.1 |

FOREIGN PATENT DOCUMENTS

| ES | 2400306 T3 * | 4/2013 | A61K 38/43 |

OTHER PUBLICATIONS

ES-2400306-T3, Attached English machine translation (89 pages) (Year: 2013).*
Sigma-Aldrich, Safety Data Sheet for anti Properdin, clone 6E9E6. Version 8.3. (Online at https://www.sigmaaldrich.com/US/en/product/mm/mabf2125) Accessed: [Jul. 6, 2023]. (Year: 2021).*
Ferreira et al., Native Polymeric forms of properdin selectively bind to targets and promote activation of the alternative pathway of complement, Immunobiology, 215, (2010), p. 932-940. (Year: 2010).*

\* cited by examiner

*Primary Examiner* — Ellen J Marcsisin
(74) *Attorney, Agent, or Firm* — MacMillan, Sobanski & Todd, LLC

(57) ABSTRACT

Methods measuring properdin function and kits for conducting ELISA Assays using anti-properdin antibodies and uses thereof are described.

6 Claims, 8 Drawing Sheets
(3 of 8 Drawing Sheet(s) Filed in Color)

ELISA ASSAY FOR MEASURING FUNCTION OF PROPERDIN AND KITS FOR CONDUCTING ELISA ASSAYS USING ANTI-PROPERDIN ANTIBODIES

CROSS-REFERENCE TO RELATED APPLICATIONS

This application claims the benefit of U.S. Provisional Application Ser. No. 62/670,314 filed May 11, 2018, the entire disclosure of which is expressly incorporated herein by reference.

STATEMENT REGARDING FEDERALLY SPONSORED RESEARCH

This invention was made with government support under Grant No. HL112937 awarded by the National Institutes of Health. The government has certain rights in the invention.

BACKGROUND OF THE INVENTION

The complement system is a well-known effector mechanism of the immune response, providing not only protection against pathogens and other harmful agents but also recovery from injury. The complement system comprises a number of proteins that typically exist in the body in inactive form. In the complement system, pathogens are cleared from the circulation either by direct killing or when they bind to complement receptors on macrophages and other immune cells. Without the complement system, the pathogens will not be eliminated effectively. In addition, complement is important for normal and pathological inflammatory reactions. Complement can be activated through 3 pathways: The classical, lectin and alternative pathways. The alternative pathway, unlike the other pathways will activate on any surface that cannot control its activation, allowing C3 fragments to be deposited on pathogens (that cannot regulate the pathway), which will be either directly killed by complement or efficiently killed by immune cells that have bound to the C3 fragments. The alternative pathway can also activate on our own cells and tissues when they are not normal (such as dead or dying) as a physiological way of tagging them for removal by immune cells. Regulation of the alternative pathway is essential for its efficient function. There are proteins the negatively regulate to avoid unwanted damage to our own cells, and there is one positive regulator known as properdin that allows the alternative pathway to be very efficient. Failure in proteins of the alternative pathway will leave the individual more susceptible to infections and dying cells that, if not cleared, may serve as sources of altered self-antigens with the potential for inducing autoantibodies. In addition, excessive complement activation (e.g. due to massive tissue damage) or failure to adequately regulate complement activity (e.g. due to mutations) will result in exaggerated complement activity, with increased inflammation and disease susceptibility.

Also, complement deficiencies comprise between 1 and 10% of all primary immunodeficiencies (PIDs) according to national and supranational registries. However, there is a great lack of awareness among clinicians and general practitioners of such deficiencies.

Also, there are only a few centers worldwide that provide a comprehensive laboratory complement analysis. This is a concern as the genetic deficiency of properdin or of the terminal pathway components (C5 to C9), are highly susceptible to fulminant, systemic meningococcal disease Clinical indications for possible complement deficiencies include recurrent mild or serious bacterial infections, autoimmune disease, or episodes of angioedema (a painless, but often dramatic, swelling under the skin, or swelling in the intestines). Potential complement-related problems also include renal disease, vasculitis (blood vessel inflammation), atypicial hemolytic uremic syndrome, paroxysmal nocturnal hemoglobinuria, and age-related macular degeneration.

Currently there is no commercially available assay to measure properdin function in biological samples. Research labs (very specialized) have been limited to using functional assays requiring fresh red blood cells, carried out in 1-3 ml glass tubes. These assays are cumbersome because they require using animal cells that have a short shelf life. Usually, the assay is carried out in 0.5 ml to 1 ml volumes, which uses high amounts of expensive reagents.

In addition, there is no ELISA-based assay that measures properdin function.

SUMMARY OF THE INVENTION

In a first aspect, there is provided herein an assay for determining the function of properdin, comprising:
  i) coating a surface with a non-inhibitory anti-properdin antibody, and incubating for a desired time and at a desired temperature;
  ii) adding a blocking agent to prevent non-specific binding and to block any remaining active sites on the surface, and incubating for a desired time and at a desired temperature;
  iii) adding a sample that contains properdin to the surface of step ii) and incubating for a desired time and at a desired temperature;
  iv) adding properdin-depleted serum to the surface of step iii); wherein the proper-depleted serum provides complement proteins including $C3(H_2O)$, C3, Factor B and Factor D, and, wherein $C3(H_2O)$ and Factor B bind to properdin, and wherein Factor D cleaves Factor B to form $C3(H_2O)Bb$ that, in turn, cleaves C3 and deposits C3b covalently on the proteins on the surface; and,
  v) adding an anti-C3b antibody to detect the C3b on the surface.

In another aspect, there is provided herein an enzyme linked immunosorbent assay (ELISA)-based method for detecting the function of properdin polymeric forms in normal and/or diseased biological samples, comprising the assay described herein.

In another aspect, there is provided herein a method for detecting nonphysiological forms of properdin (Pns) that appear during repeated freeze-thaw cycles while properdin is in storage, comprising: conducting the assay as described herein.

In certain embodiments, the sample comprises normal human serum (NHS) or serum from other species, or fluid samples from other parts of the body.

In certain embodiments, the sample comprises atypical human serum, or serum from other species, or atypical samples for other parts of the body.

In certain embodiments, the assay is used in diagnostic applications.

In certain embodiments, the assay is used in research applications.

In certain embodiments, the non-inhibitory anti-properdin antibody comprises monoclonal antibody 6E9E6.

In certain embodiments, the control sample containing properdin is added at 800 ng/ml, and the test sample is added at an unknown concentration of properdin, and incubated at 37° C.

In certain embodiments, properdin-depleted sera is diluted 1/20 or 1/18-fold in 5 mM magnesium ethylene glycol tetraacetic acid (MgEGTA).

In certain embodiments, C3b deposition is measured by adding biotinylated anti-C3b antibody and streptavidin-horseradish peroxidase.

In another aspect, there is provided herein a method of detecting properdin function comprising:
  i) obtaining a blood sample from a subject;
  ii) detecting the presence of properdin in the blood sample by contacting the blood sample with non-inhibitory anti-properdin antibody; and
  iii) detecting the binding of the non-inhibitory anti-properdin with a C3 antibody.

In another aspect, there is provided herein a method of diagnosing an alternative pathway (AP)-mediated pathology in a subject, comprising:
  i) conducting the assay described herein;
  ii) determining the level of properdin function in the sample; and,
  iii) treating the subject.

In certain embodiments, the subject has, or is suspected of having, a complement deficiency In certain embodiments, the subject has, or is suspected of having, a properdin deficiency, In certain embodiments, the subject is a human subject.

In certain embodiments, a kit is provided that comprises a non-inhibitory anti-properdin antibody.

In certain embodiments, the kit additionally comprises reagents for an enzyme-linked immunosorbent assay (ELISA) test, selected from the group comprising slides, micro-titer plates, secondary antibodies, marker enzymes and corresponding marker enzyme substrate for C3 antibody detection.

In another aspect, there is provided herein a kit for conducting an ELISA assay, comprising: at least one non-inhibitory antibody such as anti-properdin antibody (6E9E6), and at least one labelled anti-C3b antibody.

In certain embodiments, the kit includes instructions.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

PRIOR ART

DETAILED DESCRIPTION

Figure 1:
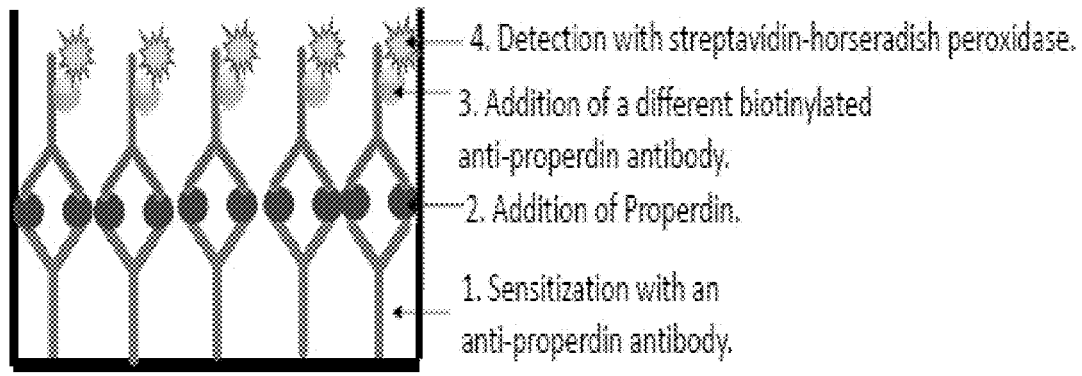
FIG. 1: Schematic illustration of a sandwich ELISA that detects the presence of properdin.

Before explaining at least one embodiment of the presently described inventive concept(s) in detail by way of exemplary drawings, description, experimentation, results, and/or laboratory procedures, it is to be understood that the inventive concept(s) is not limited in application to the details of construction and the arrangement of the methods, processes, compositions, and components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting except where indicated as such.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term unless the context clearly indicates otherwise.

As used herein, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

As used herein, the terms "optional" or "optionally" may be taken to mean that the subsequently described structure, event or circumstance may or may not occur, and that the description includes instances where the event occurs and instances where it does not.

As used herein, the term "administering" when used in conjunction with a therapeutic means to administer a therapeutic directly into or onto a target or to administer a therapeutic to a subject whereby the therapeutic positively impacts the area to which it is targeted.

The term "detect" or "detecting" is used in the broadest sense to include quantitative, semi-quantitative or qualitative measurements of a target molecule. In one aspect, methods described herein may only determine the presence or absence of a particular properdin polypeptide in a biological sample and, thus, that the properdin polypeptide is detectable or, alternatively, undetectable in the sample when assayed by the method.

As used herein, the terms "treat," "treating" or treatment" generally mean the exposure of a living organism to one or more physical, chemical or psychological entities or stimuli that may prevent, improve or ameliorate a diseased state. As used herein, the term "treating" refers to both therapeutic treatment and prophylactic or preventative measures.

As used herein, the term "indication" generally refers to a medical condition or symptoms associated with a medical condition.

As used herein, "subject" refers to any mammal, including humans, domestic and farm animals, and zoo, sports, or pet animals, such as dogs, horses, cats, sheep, pigs, cows, etc. The preferred mammal herein is a human, including adults, children, and the elderly.

As used herein, "preventing" means preventing in whole or in part, or ameliorating or controlling.

As used herein, a "therapeutically effective amount" in reference to the compounds or compositions refers to the amount sufficient to induce a sign or any other desired alteration that results in the promotion and/or improvement of a subject's health.

As use herein, the term "improves" generally means changes either the appearance, form, characteristics and/or the physical health.

General Description

The complement system is a central component of the innate immune system. It participates in direct killing of pathogens, in opsonization and removal of pathogens and altered self cells (e.g. apoptotic, necrotic, etc.), and in generation of pro-inflammatory fragments that increase vascular permeability, have potent chemotactic abilities, and can activate phagocytic, pro-inflammatory cells). The complement system can be activated by three pathways (the classical, lectin and alternative pathways).

Properdin is a highly positively charged 53 kDa glycoprotein that is the only known positive regulator of the alternative pathway of the complement system. Properdin stabilizes complement enzymes (the C3 and C5 convertases), such that their activity increases 5-10-fold, thus leading to efficient amplification of C3b deposition on the cell surfaces. Properdin is composed of seven thrombospondin repeat type I (TSRO-6) domains. Under physiological conditions properdin exists as cyclic dimers (P2), trimers (P3) and tetramers (P4) in a 26:54:20 (P2:P3:P4) ratio and the convertase stabilizing function of P4 is greater than P3 and P3 is greater than that of P2. Head-to-tail associations of four TSR domains from two monomers form a curly vertex that holds together alternative pathway (AP) convertase by interacting with both C3b and Bb. TSR4 is required for stabilizing the C3bBb convertase, TSR5 is important in C3b and sulphatide binding and, TSR6 is essential for properdin polymerization whereas TSR3 domain is not required for C3b stabilization or sulphatide binding.

In addition to its role as a regulator of the AP, properdin can also act as an initiator of the AP by selectively binding to target surfaces and providing a platform for de novo convertase assembly. Examples of such cell surfaces include zymosan, late apoptotic and necrotic cells, C. pneumoniae and activated platelets.

Nonphysiological forms of properdin (Pns) appear during repeated freeze-thaw cycles while properdin is in storage and have distinctly different properties from physiological forms since they bind non-specifically to surfaces and consume complement, even in solution.

Thus, it is essential to separate the physiological forms from the Pns by ion exchange or size exclusion chromatography to accurately assess properdin function.

Also, in humans, deficiency of properdin leads to susceptibility to bacterial infections, especially to severe fulminant meningococcal infections. Complete deficiency of properdin leads to Type I deficiency, partial deficiency leads to Type II, and Type III is due to dysfunctional properdin.

Also, properdin is now believed to play an important role in inflammatory diseases such as thromboinflammation, as demonstrated by its role in enhancing platelet granulocyte aggregate formation in thrombin receptor-activated whole blood, as well as having a role in a variety of diseases where the activation of the alternative pathway is central to the pathogenesis (e.g., atypical hemolytic uremic syndrome, paroxysmal nocturnal hemoglobinuria, and many chronic inflammatory diseases).

In normal humans, the concentration of properdin in serum ranges from about 4 to about 25 µg/ml. Various leukocytes including mast cells, monocytes, dendritic cells, T cells, neutrophils are known to produce properdin.

However, in local inflammatory microenvironments, properdin concentration may increase in response to leukocyte activation, causing inflammation due to amplification of the activity of the complement system.

Currently there is no in vitro enzyme linked immunosorbent assay (ELISA)-based method to detect the function of properdin polymeric forms in any normal or diseased biological sample.

Described herein is the use of anti-properdin monoclonal antibodies (MoAbs) in an assay that measures the function of properdin in both normal human serum (NHS) and in atypical human serum. The assay has applications in both diagnostics and research.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

The value of the present invention can thus be seen by reference to the Examples herein.

Standardization of a Properdin Functional ELISA.

FIG. 1 is a general schematic illustration of a sandwich ELISA that detects properdin with maximum sensitivity. In order to be able to measure properdin levels in biological samples, a highly sensitive sandwich ELISA using anti-properdin monoclonal antibodies was standardized, where one monoclonal antibody has been biotinylated.

Isolation of Properdin Forms.

Physiological polymeric forms of properdin dimers (P2), trimers (P3), and tetramers (P4) were separated from non-physiological aggregated properdin (Pns) by size exclusion chromatography. Briefly, properdin (5 mg) was loaded onto a Phenomenex Bio Sep-Sec-S4000 column (600×7.8 mm) with a guard column (75×7.8 mm), and was eluted at a flow rate of 0.5 ml/min in PBS. Purified, physiological and non-physiological forms of properdin were stored at 4° C. and used within three weeks of separation.

Standardization of the Functional ELISA Using Properdin Forms.

In order to standardize the functional ELISA, a series of experiments were conducted where 96 well plates were coated with varying concentrations (1-20 µg/ml) of non-inhibitory MoAbs 1G6D2 or 6E9E6 in PBS (100 µl/well) and then incubated overnight at 4° C.

"1G6D2" monoclonal antibody is available from Hycult-Biotech, under Catalog #: HM2354-FS.

"6E9E6" monoclonal antibody is available from Millipore Sigma, under Cat. No. MABF2125.

The plates were washed four times with PBS/0.05% TWEEN® (250 µl/well). PBS/3% BSA (250 µl/well) was added to block remaining active sites and the plates were incubated for 2 hours at 37° C., followed by 2 washes with PBS/0.05% Tween (250 µl/well). Properdin forms [P2, P3, P4, or pooled P2-P4 at a 1:2:1 ratio as found in NHS, or Pn, or Punfrac (pure properdin with physiological P2-P4 polymers and non-physiological aggregates/unfractionated properdin)] were diluted in PBS/1% BSA/0.05% TWEEN® and added at varying concentrations of 0-1000 ng/ml (100 µl/well). The plates were then incubated for 1 hour at 37° C. followed by 4 washes with PBS/0.05% TWEEN® (250 µl/well).

Next, properdin-depleted sera in varying dilutions (1/10-1/1000-fold) was added in GVB=+5 mM MgEGTA (100

μl/well). GVB=+20 mM EDTA was added at varying time points between 0-90 minutes to stop the reaction followed by 4 washes with PBS/0.05% TWEEN® (250 μl/well).

The C3b deposited covalently on the proteins in the plates was detected by incubating with varying concentrations (1/2000-1/10000) of biotinylated anti-C3b antibody (100 μl/well) at 37° C. for 1 hour followed by 4 washes with PBS/0.05% TWEEN® (250 μl/well). Streptavidin-horseradish peroxidase at 1/5000 (100 μl/well) was added and incubated at 37° C. for 45 minutes followed by 4 washes with PBS/0.05% TWEEN® (250 μl/well) and then ABTS substrate was added and the absorbance of each well was measured at 405 nm using a Tecan Infinite M200 spectrophotometer.

Figure 2:
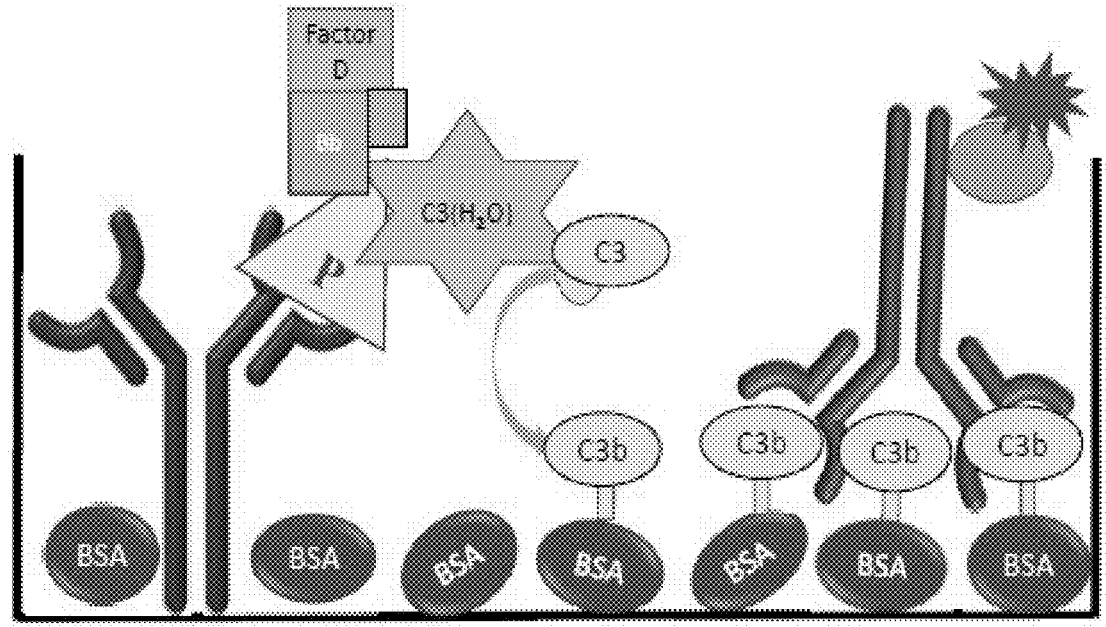
FIG. 2: Schematic illustration of a properdin functional ELISA. A plate is coated with a non-inhibitory anti-properdin MoAb (in red) and then incubated overnight at 4° C. The plate is blocked with PBS/3% BSA (in purple) to block the remaining active sites and incubated for 2 hours at 37° C. Properdin (light blue) is added and the plate is incubated for 1 hour at 37° C. Next, properdin depleted serum is added, which provides complement proteins including $C3(H_2O)$ (green), Factor B and Factor D (orange). $C3(H_2O)$ and Factor B bind to properdin, Factor D cleaves Factor B to form $C3(H_2O)$Bb (de novo convertase formation on properdin) that can cleave C3 and deposit C3b (yellow) covalently on the proteins in the plate and the C3b is detected with a specific antibody (blue).

FIG. 2 is a schematic illustration showing a plate is coated with a non-inhibitory anti-properdin MoAb (in red); blocked with PBS/3% BSA (in purple) to block the remaining active; addition of properdin (light blue); addition of properdin depleted serum, which provides complement proteins including $C3(H_2O)$ (green), Factor B and Factor D (orange). $C3(H_2O)$ and Factor B bind to properdin, Factor D cleaves Factor B to form $C3(H_2O)Bb$ (de novo convertase formation on properdin) that can cleave C3 and deposit C3b (yellow) covalently on the proteins in the plate and the C3b is detected with a specific antibody (blue).

Evaluation of Properdin Forms in their Ability to Initiate C3b Deposition in a Functional ELISA.

A 96 well plate was coated with 10 μg/ml 6E9E6 (non-inhibitory anti-properdin MoAb) or 6E11A4 (inhibitory anti-properdin MoAb) in PBS (100 μl/well) and then incubated overnight at 4° C. The plate was washed four times with PBS/0.05% TWEEN® (250 μl/well). PBS/3% BSA (250 μl/well) was added to block the remaining active sites and the plate was incubated for 2 hours at 37° C., followed by 2 washes with PBS/0.05% TWEEN® (250 μl/well). Properdin (P2, P3, P4, or pooled P2-P4 at a 1:2:1 ratio as found in NHS, or Pn, or Punfrac) was diluted in PBS/1% BSA/0.05% TWEEN® added at 800 ng/ml (100 μl/well). The plate was then incubated for 1 hour at 37° C. followed by 4 washes with PBS/0.05% TWEEN® (250 μl/well).

Next, properdin-depleted sera (either 1/20 or 1/18, depending on the serum batch) was added in GVB=+5 mM MgEGTA, required for AP activity (100 μl/well). The reaction was stopped with GVB=+20 mM EDTA at 0-90 minutes followed by four washes with PBS/0.05% TWEEN® (250 μl/well). The C3b deposited covalently on the proteins in the plate was detected by incubating with a biotinylated anti-C3b antibody 1/5000 (100 μl/well) at 37° C. for 1 hour followed by 4 washes with PBS/0.05% TWEEN® (250 μl/well). Streptavidin-horseradish peroxidase at 1/5000 (100 μl/well) was added and incubated at 37° C. for 45 minutes followed by 4 washes with PBS/0.05% TWEEN® (250 μl/well) and then ABTS substrate was added and the absorbance of each well was measured at 405 nm using a Tecan Infinite M200 spectrophotometer.

Evaluation of Biological Samples in the Functional ELISA.

Determination of the Activity of Properdin in NHS Using Functional ELISA.

The assay was carried out as described above, with the following exceptions: after the blocking step, properdin (P2, P3, P4, P2-P4 at a 1:2:1 ratio, Pn, Punfrac) at 800 ng/ml in PBS/1% BSA/0.05% TWEEN® or NHS (Innovative Research or Comptech) at a dilution that provides 800 ng/ml of properdin diluted in 20 mM EDTA+PBS/1% BSA/0.05% TWEEN®, was added at 100 μl/well. The NHS were added in 20 mM EDTA to avoid complement activation during this properdin recruitment step.

The plate was then incubated for 1 hour at 37° C. followed by 4 washes with PBS/0.05% TWEEN® (250 μl/well). Next, 1/18 dilution of properdin-depleted sera was added in GVB=+5 mM MgEGTA, required for AP activity (100 μl/well).

The reaction was stopped with GVB=+20 mM EDTA at 0-120 minutes followed by four washes with PBS/0.05% TWEEN® (250 μl/well).

Results

Standardization of a Properdin Functional ELISA.

Separation of Properdin Forms.

Non-physiological aggregates of properdin ($P_n$) accumulate in purified properdin preparations, due to prolonged storage and freeze/thaw cycles, are artificially highly active and should be removed before use in research.

Properdin deficiency leads to increased susceptibility to meningitis and gonorrhea (systemic, recurrent Neisserial infections). In type III deficiency there is a normal concentration of protein, but without function.

The alternative pathway of complement participates in the pathogenesis of many inflammatory diseases (including cardiovascular and autoimmune, etc.) and research is needed to understand properdin (positive AP regulator) function in disease settings.

Figure 3A:
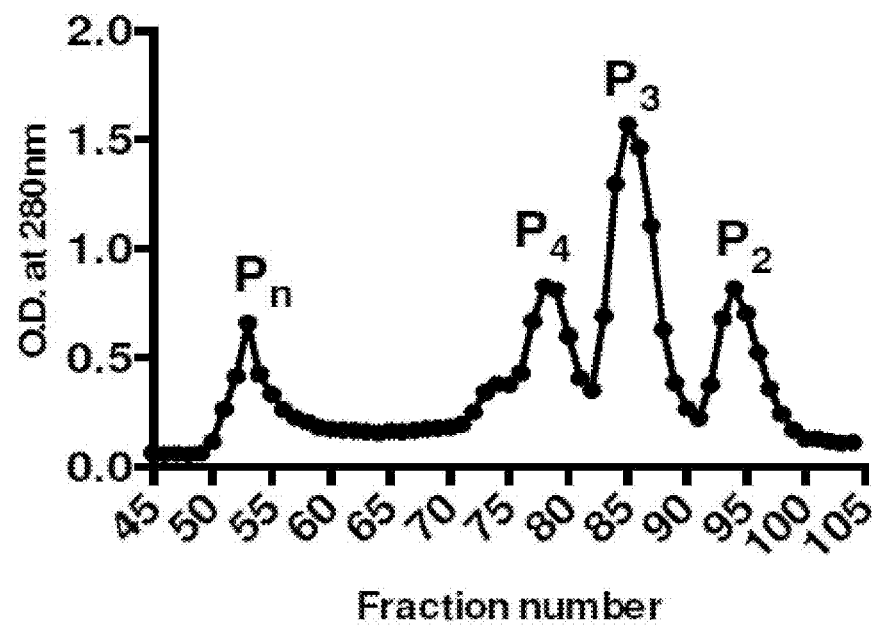
FIG. 3A: Physiological forms of properdin; dimers (P2), trimers (P3) and tetramers (P4) were separated from each other and from the nonphysiological aggregates (Pn) by size exclusion chromatography. The graph shows the O.D. values for fractions containing the properdin forms as labelled in FIG. 3A. The graph is a representative of 3 independent experiments.
Figure 3B:
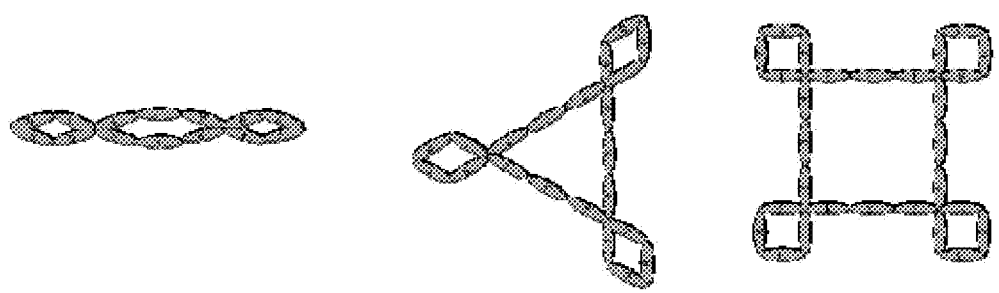
FIG. 3B: Schematic illustration of properdin protein that exists in dimers (P2), left; trimers (P3), middle; and, tetramers (P4), right.

In order to be able to standardize the properdin functional ELISA using properdin forms, physiological forms of properdin dimers (P2), trimers (P3) and tetramers (P4) were separated from each other and from the non-physiological aggregates (Pns), that appear during repeated freeze-thaw cycles, by size exclusion chromatography (FIG. 3A). FIG. 3B provides a schematic illustration of properdin protein that exists in dimers (P2), left; trimers (P3), middle; and, tetramers (P4), right.

Standardization of the Functional ELISA Using the Properdin Forms.

In order to standardize a functional ELISA for properdin (see FIG. 2), preferred reagents and concentrations to use for the assay were determined: (a) which non-inhibitory MoAb is useful to use for capturing the properdin from samples and what a preferred concentration would be; (b) what concentration of properdin would give a preferred functional signal; (c) what dilution of properdin-depleted serum is preferred; (d) what is the preferred concentration of biotinylated anti-C3b antibody to use is; and (e) what the preferred time range that allows for detecting functional differences between the properdin forms is.

A series of standardization experiments were performed where all the above-mentioned parameters were varied and the data indicated that:
  (a) the MoAb that detected the most differences between properdin forms function was 6E9E6 at 10 μg/ml;
  (b) the function of properdin (i.e., C3b deposition) is consistently detected with 800 ng/ml of properdin;
  (c) the dilution of properdin-depleted serum is useful at 1/20 or 1/18 depending on the batch of serum used;
  (d) the concentration of biotinylated anti-C3b antibody dilution is useful at 1/5000; and
  (e) the time points where properdin function could be consistently detected was 0-90 min. Results for the basic standardization are not shown.

In order to standardize the functional ELISA; varying the concentration of the sensitization antibody, properdin, the dilution of p-depleted sera, dilution of anti-c3b antibody were varied, as shown in Table 1 below. All these parameters were measured at varying timepoints. Example 1 shows one embodiment that uses the sensitization antibody at 10 ug/ml, properdin between 300 and 800 ng/ml, p-depleted sera at 1/20 or 1/18 fold dilution depending on sera lot, and 1/5000 dilution of anti-c3b antibody.

TABLE 1

| Steps of the functional ELISA | Concentrations/ dilution/ time range | Example 1 = Concentrations/ dilutions/time range |
|---|---|---|
| Sensitization antibody | 1-20 µg/ml | 10 µg/ml |
| Properdin | 0-1000 ng/ml | 400-800 ng/ml |
| Properdin-depleted sera | 1/10-1/1000-fold | 1/18 or 1/20-fold |
| Biotinylated anti-C3b antibody | 1/2000-1/10000 | 1/5000 |
| Time range | 0-90 minutes | 0-90 minutes |

The protocol for the final standardized properdin functional assay as well as data for the differences in function between the properdin forms, as detected in the functional assay, are described below.

Evaluation of Properdin Forms in their Ability to Initiate C3b Deposition in a Functional ELISA.

Figure 4A:
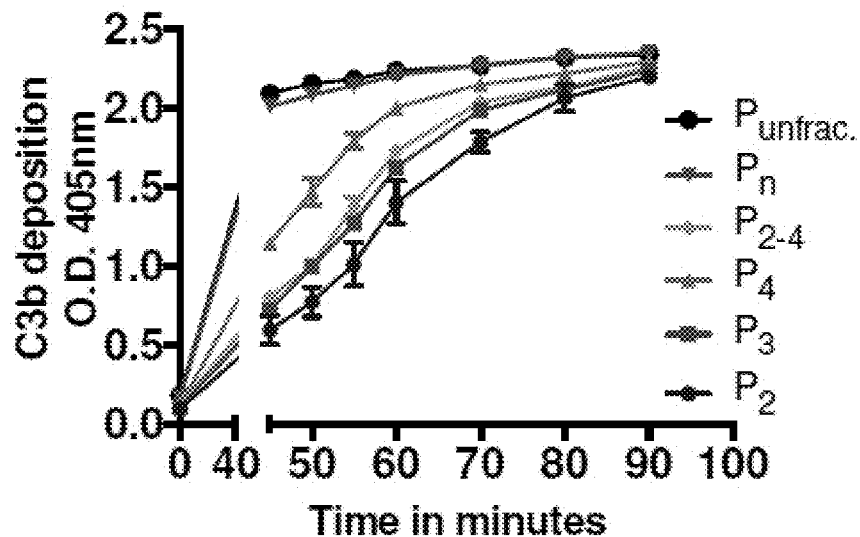
FIG. 4A: Functional ELISA with properdin forms and non-inhibitory anti-properdin MoAb 6E9E6. A 96 well plate was coated with 10 μg/ml of 6E9E6 and then incubated overnight at 4° C. The plate was then blocked with PBS/3% BSA for 2 hours at 37° C. Properdin forms were added at 800 ng/ml and plate was incubated for 1 hour at 37° C. Properdin-depleted sera was diluted 1/20 or 1/18-fold in 5 mM magnesium ethylene glycol tetraacetic acid (MgEGTA)-required for AP function, and added to the wells. The reaction was stopped at various times between 0-90 minutes, by adding 20 mM ethylenediaminetetraaceticacid (EDTA). C3b deposition was measured by adding biotinylated anti-C3b antibody and streptavidin-horseradish peroxidase. Finally, ABTS substrate (ABTS (2,2'-Azinobis [3-ethylbenzothiazoline-6-sulfonic acid]-diammonium salt) is a water-soluble HRP substrate that yields a green end product upon reaction with peroxidase) was added and the absorbance of each well at 405 nm was measured. The graph is representative of 4 independent experiments. Results are shown as mean and SD of duplicate observations.

In order to validate the functional ELISA, different properdin forms were tested (which exhibit differences in their ability to promote complement activation (Pn>P4>P3>P2). The functional ELISA was performed using the non-inhibitory anti-properdin MoAb 6E9E6 (see method schematic in FIG. 2), and the function of the different properdin forms was measured at various time points between 0-90 minutes (FIG. 4A).

Figure 4B:
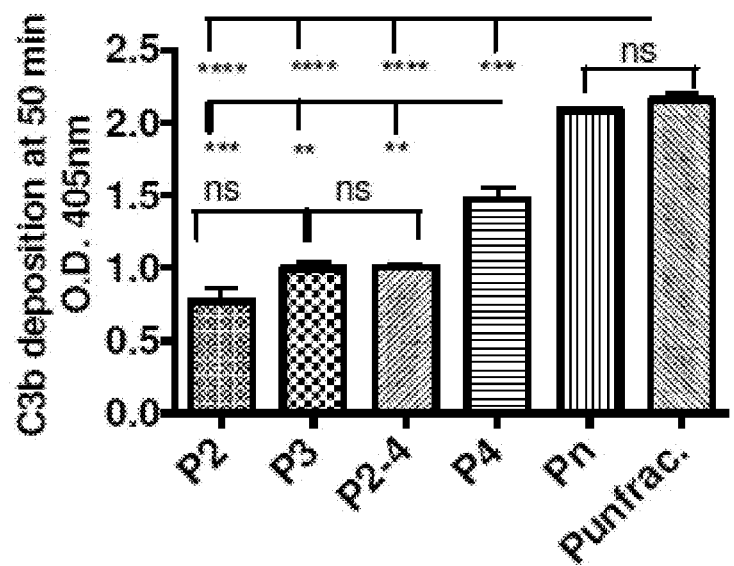
FIG. 4B: C3b deposition at 50 minutes. This is the optimal time point for reading the assay. The significance of differences in C3b deposition between properdin forms at 50 minutes was assessed by one-way ANOVA with Tukey's multiple comparison test; $p<0.0001**$, $p<0.001*$, $p<0.01**$, $p>0.05$ ns.

The data shows that all properdin sources tested led to deposition of C3b in a time-dependent manner. Between 45-55 minutes Punfrac (which is pure properdin that contains physiological P2-P4 polymers and non-physiological aggregates), and Pn had significantly higher activity than all the physiological forms of properdin (FIG. 4A). In addition, P4 showed a significantly higher activity than P3 and P2 (FIG. 4B).

Figure 5:
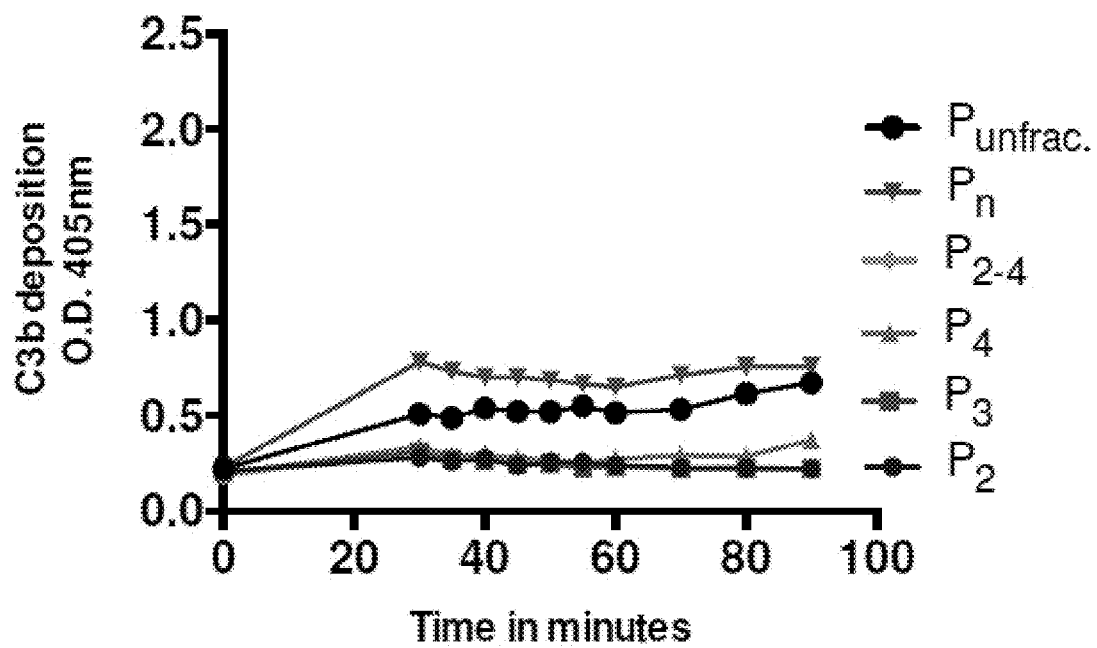
FIG. 5: The functional ELISA with properdin forms does not work if the anti-properdin MoAb is inhibitory (i.e. 6E11A4). The functional assay will not work if the anti-properdin antibody is inhibitory (i.e., inhibits properdin function). Thus, one of the particular requirements for the assay is to use a non-inhibitory anti-properdin antibody. A 96 well plate was coated with 10 μg/ml of 6E11A4 and then incubated overnight at 4° C. The plate was then blocked with PBS/3% BSA for 2 hours at 37° C. Properdin forms were added at 800 ng/ml and plate was incubated for 1 hour at 37° C. Properdin-depleted sera was diluted 1/20-fold in 5 mM MgEGTA (required for AP function) and added to the wells. The reaction was stopped at various times between 0-90 minutes, by adding 20 mM EDTA. C3b deposition was measured by adding biotinylated anti-C3b antibody and streptavidin-horseradish peroxidase. Finally, ABTS substrate was added and the absorbance of each well at 405 nm was measured. The experiment was performed once. Results are shown as single observations. No dose-dependent increase in C3b deposition is observed.

The inhibitory anti-properdin MoAb 6E11A4 could no longer detect the differences between the functions of the physiological forms of properdin (FIG. 5); while not wishing to be bound by theory, it is now believed that this is due to the functional inhibition of the captured properdin, although, there was some C3b deposition with the Pn and Punfrac.

Evaluation of Biological Samples in the Functional ELISA

Functional ELISA with NHS.

Figure 6:
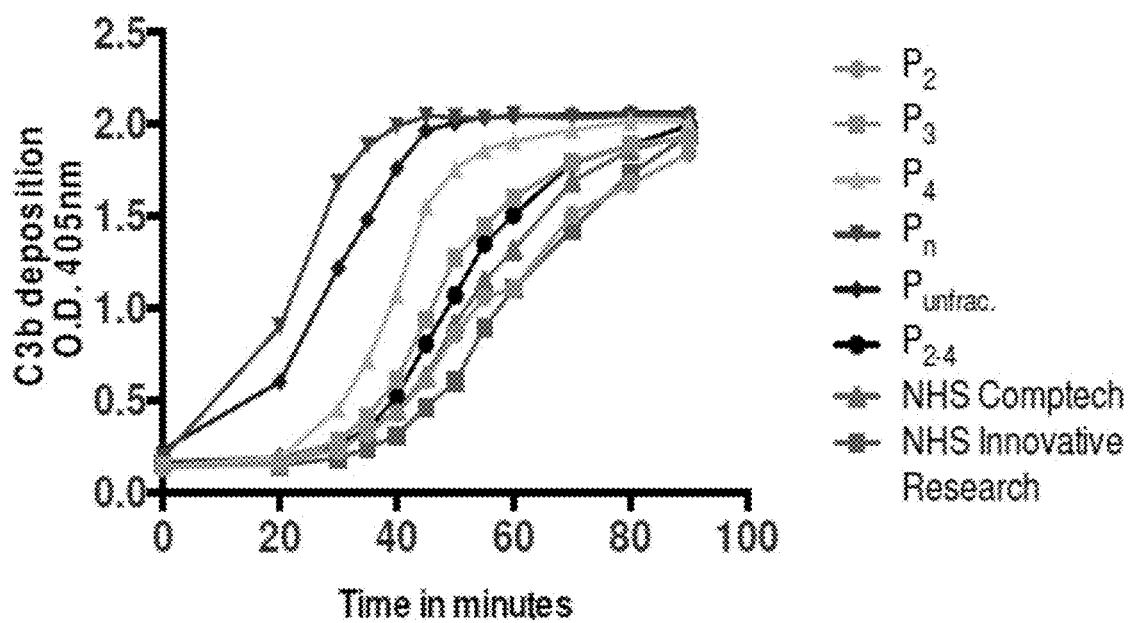
FIG. 6: Normal human serum (NHS) and properdin forms lead to a time-dependent deposition of C3b in the functional ELISA. A 96 well plate was coated with 10 μg/ml of 6E9E6 and then incubated overnight at 4° C. The plate was then blocked with PBS/3% BSA for 2 hours at 37° C. Properdin forms and NHS with 20 mM EDTA were added at 800 ng/ml and plate was incubated for 1 hour at 37° C. Properdin-depleted sera was diluted 1/18-fold in 5 mM MgEGTA (required for AP function). The reaction was stopped at various times 0-90 minutes, by adding 20 mM EDTA. C3b deposition was measured by adding biotinylated anti-C3b antibody and streptavidin-horseradish peroxidase. Finally, ABTS substrate was added and the absorbance of each well at 405 nm was measured. The graph is a representative of 3 separate experiments. Results are shown as single observations.

The function of properdin in the context of NHS was evaluated in parallel with different properdin forms (individual properdin forms, P2-P4 pool, and Pn) and with Punfrac. All samples were tested at an equivalent concentration of 800 ng/ml. When the function of properdin was tested between 0 and 90 minutes, NHS from two sources and all the properdin forms tested resulted in deposition of C3b in a time-dependent manner (FIG. 6). The C3b deposition with the NHS was more similar to the physiologicalproperdin forms (in particular P2) than to Punfrac or Pn. The experiment was repeated 3 times with different time points, and the trend was consistent in all experiments. The results show that the functional ELISA is useful to detect the function of properdin in NHS.

Figure 7:
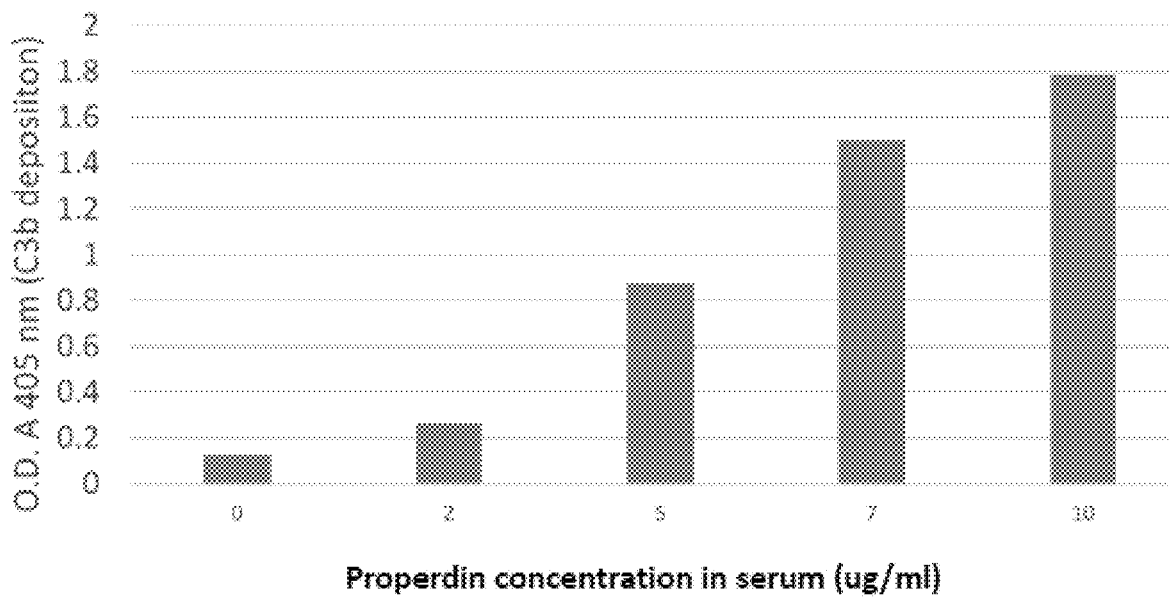
FIG. 7: The functional properdin ELISA detects differences in activity between sera that have different properdin concentrations. Assay was carried out as described in FIG. 6, except that the sera tested had varying amounts of properdin.

FIG. 7 shows that the functional properdin ELISA assay detects differences in activity between sera that have different properdin concentrations.

The method described herein provides a standardized assay which allows for the ability to measure function of properdin. It is now shown herein that this function is directly proportional to the concentration of properdin. Also shown herein are preferred time to measure function in human serum samples. The functional properdin ELISA assay is comparable to the in vitro red blood cell functional assay.

Kits

A kit for such functional properdin ELISA assay can include, for example:

1) a non-inhibitory antibody such as anti-properdin antibody (6E9E6), and
2) labeled anti-C3b antibody (commercial-source).

Instructions can also be included to note that properdin-depleted sera (requires −80° C. storage. Alternatively, instructions can be included for on-site reconstitution of lyophilized properdin-depleted sera.

The instructions can also note that properdin for control wells (requires −80° C. storage (or potential lyophilization).

Other optional components of the kit include: a buffer; detectable labels; etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Uses

The functional properdin ELISA assay is particularly useful for screening patient samples that have a low or no alternative pathway activity (AP50). As shown in FIG. 7, the result is proportional to the amount of properdin in the patient sera sample. Such assay simultaneously measures total AP50 activity just by adding the patient sample without EDTA, as well as can simultaneously measure the exact concentration of properdin in wells that receive another anti-properdin monoclonal antibody (such as 1G6D2) instead of the properdin-depleted sera, which would detect if the lack of function is due to lack of properdin in the sample.

The functional properdin ELISA assay is particularly useful for the detection of aggregates in purified properdin preparation (research) where it is important to distinguish between the aggregates and the physiological P forms since the commercially available properdin has both aggregates and the physiological P forms.

The final characterization step involved determining the species specificity of the monoclonal antibodies, using a modified alternative pathway hemolysis assay. The animal species whose properdin is recognized by the monoclonal antibodies can be used as experimental animal model for assessing properdin function in vivo.

Figure 8A:
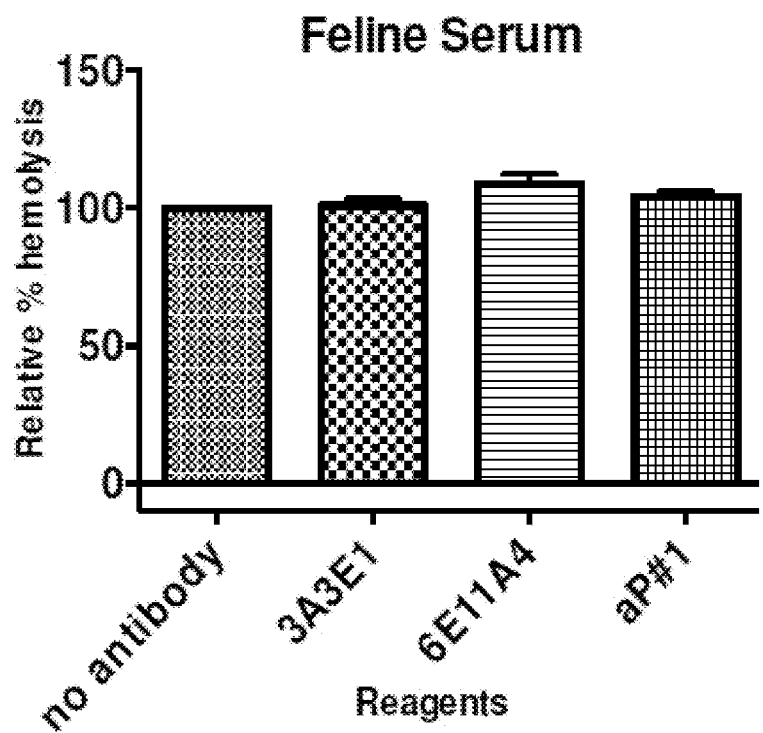
FIG. 8A: Properdin from feline serum is not recognized by the monoclonal antibodies.
Figure 8B:
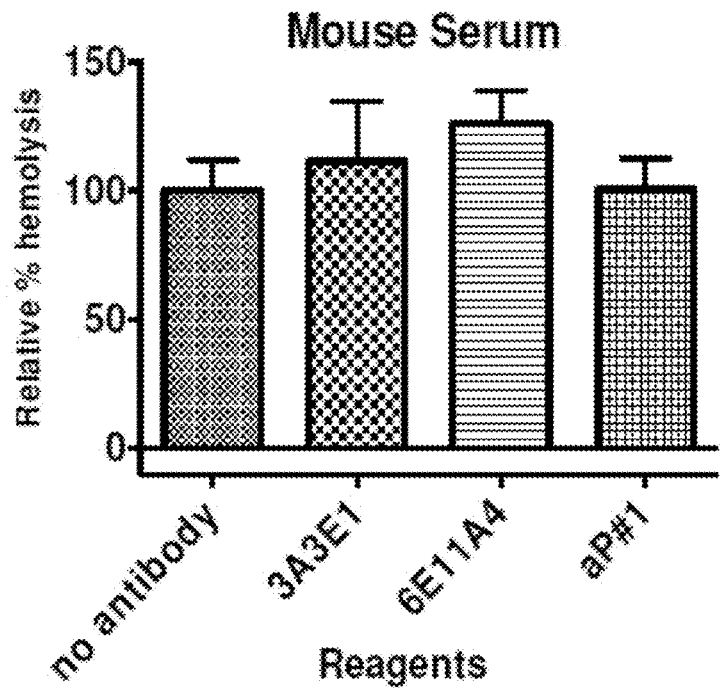
FIG. 8B: Properdin from mouse serum is not recognized by the monoclonal antibodies.
Figure 8C:
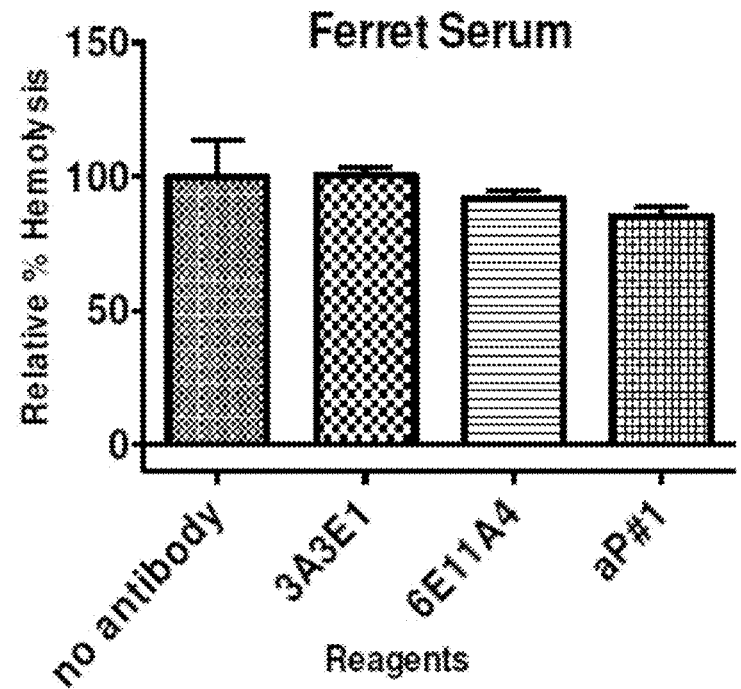
FIG. 8C: Properdin from ferret serum is not recognized by the monoclonal antibodies.
Figure 8D:
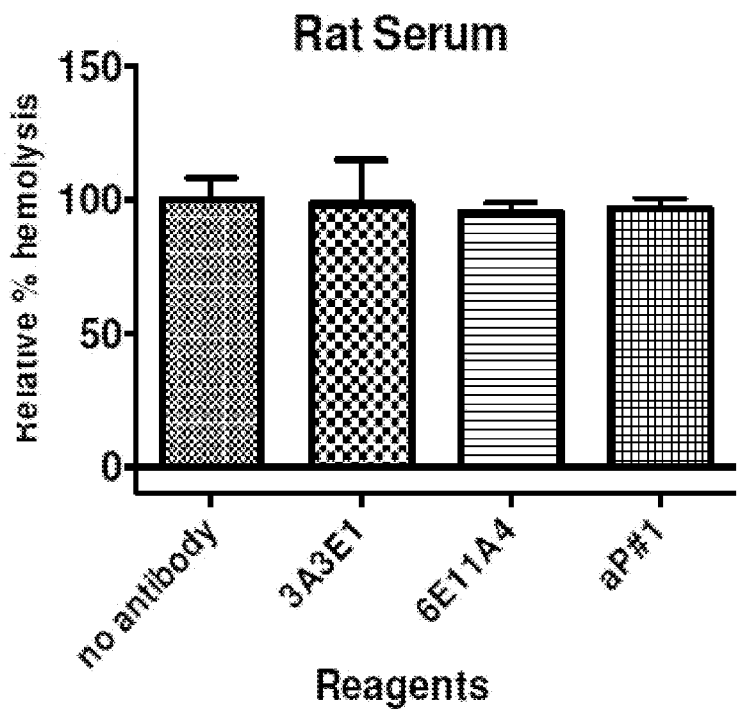
FIG. 8D: Properdin from rat serum is not recognized by the monoclonal antibodies.

Sheep erythrocytes (ES), which are normally protected by Factor H, were suspended in GVB= at approximately $1\times10^9$ cells/ml. In each tube, ES ($5\times10^6$ cells/tube) in 5 mM MgEGTA or 10 mM EDTA, were incubated with PBS, recombinant competitive inhibitor of Factor H C-terminal domains 19-20 (rH19-20) (0-8.5 µM), and animal serum (i.e. rat, mouse, rabbit, guinea pig, goat, baboon, feline, ferret and canine) at a 40% concentration, in a total volume of 24 µl, for 20 minutes at 37° C. The tubes were then placed on ice and 200 µl cold GVBE was added to each tube to stop the reaction. The tubes were spun at 2000 g for 3 minutes at 4° C. The absorbance (Abs) of 200 µl of each supernatant was measured in a microtiter plate at 414 nm. The hemolytic activity was expressed as a % of hemolysis using the following equation: % of Hemolysis=[(Abs sample-Abs control)/(Abs maximum-Abs control)]×100. The "Abs sample" is the ES in 5 mM MgEGTA with or without rH19-20+PBS. The "Abs maximum" is the ES in 5 mM MgEGTA with $H_2O$+PBS (maximum lysis control). The "Abs control" is ES in 10 mM EDTA+PBS+rH19-20. After graphing the results, the concentration of rH19-20 required to cause approximate 50% hemolysis was determined. An absence of lysis in the presence of the anti-properdin antibodies indicates that the properdin from the serum of the tested species is recognized by the anti-properdin antibody For example, properdin from feline serum (FIG. 8A), mouse serum (FIG. 8B), ferret serum (FIG. 8C) and rat serum (FIG. 8D) are not recognized by the monoclonal antibodies.

Figure 9A:
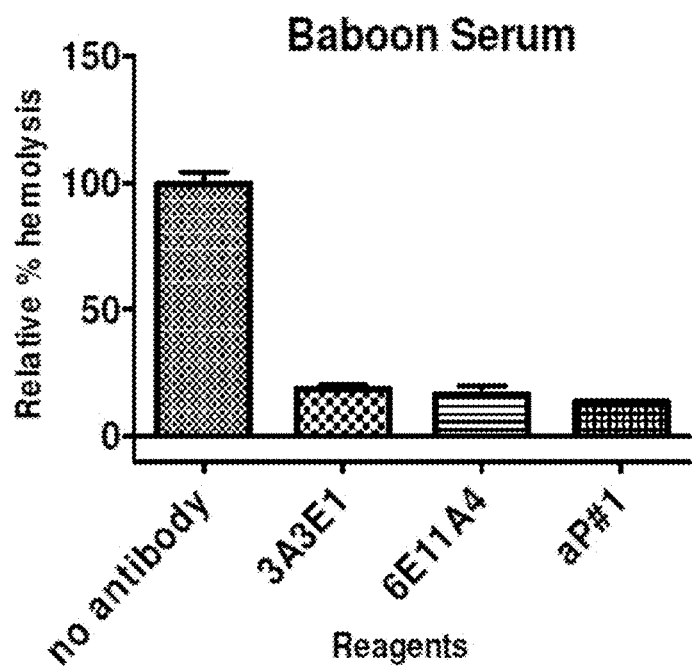
FIG. 9A: Properdin from baboon serum is recognized by the monoclonal antibodies.
Figure 9B:
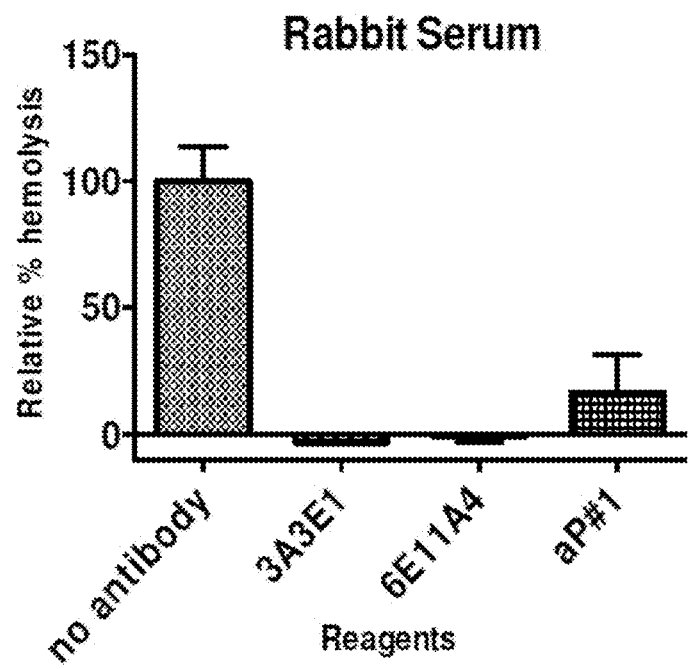
FIG. 9B: Properdin from rabbit serum is recognized by the monoclonal antibodies.
Figure 9C:
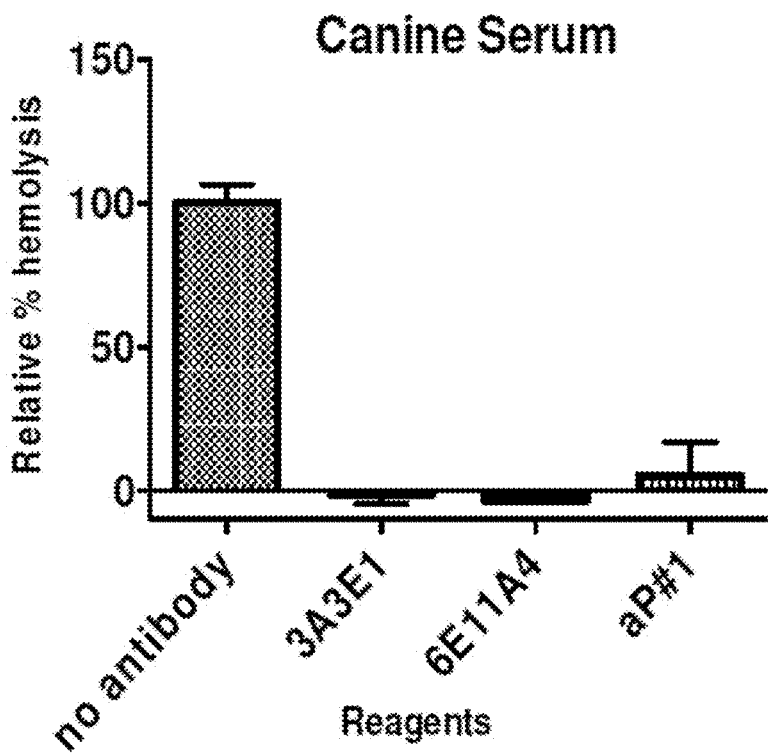
FIG. 9C: Properdin from canine serum is recognized by the monoclonal antibodies.

In contrast, properdin from baboon serum (FIG. 9A), rabbit serum (FIG. 9B) and canine serum (FIG. 9C) are recognized by the monoclonal antibodies.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method for conducting an enzyme linked immunosorbent assay (ELISA) for detecting the activity of properdin, the method comprising:
   i) coating a surface with a non-inhibitory anti-properdin antibody, and incubating for a first desired time and at a first desired temperature;
   ii) adding a blocking agent to prevent non-specific binding and to block any remaining active sites, and incubating for a second desired time and at a second desired temperature;
   iii) adding a normal human serum sample that contains properdin to the surface of step ii), wherein the normal human serum that contains properdin is added in ethylenediaminetetraacetic acid (EDTA), and incubating for a third desired time and at a third desired temperature;
   iv) adding a properdin-depleted serum sample to the surface of step iii), wherein the properdin-depleted serum sample provides complement proteins including $C3(H_2O)$, Factor B, and Factor D, and,
   wherein $C3(H_2O)$ and Factor B bind to properdin, and wherein Factor D cleaves Factor B to form $C3(H_2O)Bb$ that, in turn, cleaves C3 and deposits C3b covalently on the blocking agent on the surface; and
   v) adding an anti-C3b antibody to detect the C3b on the blocking agent on the surface.

2. The method of claim 1, further comprising removing nonphysiological forms of properdin (Pns) from the normal human serum sample by size exclusion chromatography prior to adding the normal human serum sample to the surface of step ii).

3. The method of claim 1, wherein the non-inhibitory anti-properdin antibody comprises a monoclonal antibody.

4. The method of claim 1, wherein the normal human serum sample containing properdin is added at 800 ng/ml.

5. The method of claim 1, wherein the properdin-depleted serum sample is diluted 1/20 or 1/18-fold in 5 mM magnesium ethylene glycol tetraacetic acid (MgEGTA).

6. The method of claim 1, wherein C3b deposition is measured by adding biotinylated anti-C3b antibody and streptavidin-horseradish peroxidase.

\* \* \* \* \*